| United States Patent [19] | [11] | 4,230,860 |
|---|---|---|
| Raghu | [45] | Oct. 28, 1980 |

[54] PROCESSES FOR THE SEPARATION OF ENANTIOMERS BY SELECTIVE CRYSTALLIZATION

[75] Inventor: Sivaraman Raghu, Norwalk, Conn.

[73] Assignee: American Cyanamid Company, Stamford, Conn.

[21] Appl. No.: 958,215

[22] Filed: Nov. 6, 1978

[51] Int. Cl.$^3$ .................... C07D 453/04; C07B 19/00
[52] U.S. Cl. ................................. 546/134; 562/401; 562/402; 562/505
[58] Field of Search ...................... 562/505, 401, 402; 546/134

[56] References Cited

U.S. PATENT DOCUMENTS

| 3,463,786 | 8/1969 | Bullock et al. ........................ 548/154 |
| 3,492,347 | 1/1970 | Chemerda et al. ............... 562/401 X |
| 3,636,093 | 1/1972 | Hoinowski et al. .................. 562/401 |
| 3,758,559 | 9/1973 | Bollinger ........................ 562/401 X |
| 3,794,655 | 2/1974 | Schubel et al. .................. 562/401 X |
| 3,949,000 | 4/1976 | Violet ............................ 260/606.5 P |
| 3,988,365 | 10/1976 | Gallegra ................................. 562/401 |
| 4,005,088 | 1/1977 | Gubbels et al. .................. 562/401 X |

FOREIGN PATENT DOCUMENTS 977373 11/1975 Canada .

OTHER PUBLICATIONS

Goldsworthy, *J. Chem. Soc.*, 125, 2012, (1924).
Coyner et al., *J. Am. Chem. Soc.*, 71, 324, (1949).
Kagan, *Pure and Applied Chem.*, 43, 401, (1976).

*Primary Examiner*—Natalie Trousof
*Assistant Examiner*—Vera C. Clarke
*Attorney, Agent, or Firm*—Harry H. Kline

[57] ABSTRACT

Processes for separating racemic trans-1,2-cyclic dicarboxylic acids by dissolving the racemic acid and a resolving agent such as cinchonidine in a solvent and cooling the solvent to form crystals rich in d-trans-1,2-cyclobutane dicarboxylic acid, the d-trans acid being recovered for use in preparing optically active materials.

8 Claims, No Drawings

PROCESSES FOR THE SEPARATION OF ENANTIOMERS BY SELECTIVE CRYSTALLIZATION

BACKGROUND OF THE INVENTION

The present invention relates to processes for resolving enantiomers contained in racemic mixtures, and more particularly, it relates to single-step methods for resolving racemic mixtures of trans-1,2-cyclobutane dicarboxylic acid utilizing a simple crystallization.

The synthesis of L-(−)-tetramisole, also known as "levamisole", is of great commercial interest because of its great activity as an anthelminthic, as disclosed in U.S. Pat. No. 3,463,786. One newly discovered process for preparing levamisole is a catalytic asymmetric synthesis through reduction of prochiral intermediates. The asymmetric reduction is achieved through catalysis by homogeneous asymmetric rhodium complexes acting on prochiral 1,4-disubstituted-4-imidazolin-2-ones. The maximum enantio-selectivity shown was a 33% enantiomeric excess attained with a catalyst system derived from (+)-DIOP (isopropylidine dihydroxy-2,3-bis(diphenylphosphino)-1,4-butene) and [Rh(COD)Cl$_2$] acting on 1-(2-methoxyethyl)-3-acetyl-4-phenyl-4-imidazolin-2-one. The reduced product is converted to levamisole with retention of chirality.

Reduction of various substituted prochiral olefins using homogeneous asymmetric complexes of rhodium (I) salts as catalysts is a field that has been extensively examined in recent years. A review of the state of this art by H. B. Kagan has recently appeared in *Pure and Applied Chem.*, 43, 401 (1976). For specific prochiral substrates the degree of enantioselectivity achieved in reduction has been found to be strongly influenced by the choice of the asymmetric tertiary phosphine derivative employed as a ligand in the catalyst complex. Different prochiral substrates have been found to require different asymmetric catalyst ligands for maximum enantioselectivity in catalytic reduction.

Exemplary of the use of bisphosphine-rhodium complexes as catalysts are the following:

U.S. Pat. No. 3,949,000 shows asymmetric diphosphines which, when reacted with rhodium-halogen salt, produces a rhodium complex. The rhodium complex is then used as a catalyst for the hydrogenation of precursors of amino acids.

Canadian Pat. No. 977,373 shows rhodium coordination complexes, containing phosphine and at least one halogen ion, wherein the optical activity of the complex resides in the phosphine ligand. These complexes are useful as catalysts in the asymmetric hydrogenation of α-amino acids using a chiral diphosphine rhodium complex as a homogeneous catalyst.

The greatest enantioselectivity has thus far been attained in the asymmetric reduction of prochiral 1,4-disubstituted-4-imidazolin-2-ones using the asymmetric cyclobutyl-diphosphine set forth in U.S. Pat. No. 3,949,000. Further, the use of the dextrorotatory isomer of the phosphine in complexation with rhodium as catalyst provides the S-1,4-disubstituted-2-imidazolidones in excess, necessary for the production of levamisole (S-2,3,5,6-tetrahydro-6-phenylimidazo-[2,1-b]-thiazole). The levorotatory isomer of the phosphine provides the undesired R isomer of the product.

The aforesaid U.S. patent shows the preparation of the d and l isomers of the asymmetric phosphine starting from the d and l isomers of the trans-1,2-cyclobutane dicarboxylic acid, respectively, and these in turn were obtained by the resolution of d,1-trans-1,2-cyclobutane dicarboxylic acid according to the procedure of Coyner and Hillman, *J. Am. Chem. Soc.*, 71, 324 (1949).

A consideration of the literature shows two publications concerning the resolution of racemic trans-1,2-cyclobutane dicarboxylic acid, namely, L. J. Goldsworthy, *J. Chem. Soc.*, 125, 2012 (1924) and E. C. Coyner and W. S. Hillman, *J. A.m. Chem. Soc.*, 71, 324 (1949). Both of these prior processes utilize l-quinine as a resolving agent, and this provides 1-trans-1,2-cyclobutane dicarboxylic acid in high purity.

The d-isomer of the acid, however, could be obtained from the mother liquor only in low optical purity, and several tedious recrystallizations were necessary for obtaining the pure d-isomer of the acid. Thus, these prior art processes are impractical for obtaining the high-purity d-isomer of the cyclobutane diphosphine needed for catalytic asymmetric synthesis of levamisole.

THE INVENTION

It has now been discovered that a one-step resolution of racemic trans-1,2-cyclobutane dicarboxylic acid can provide d-trans-1,2-cyclobutane dicarboxylic acid in high purity. The novel process of this invention can thus overcome disadvantages of prior art processes in giving the unwanted isomer or in requiring long, tedious, low-yield recrystallizations of partially enriched d-acids obtained from mother liquors.

Briefly, the present invention provides novel processes for the preparation of d-trans-1,2-cyclobutane dicarboxylic acid by resolving a racemic mixture, which processes comprise dissolving the racemic trans-dicarboxylic acid and a resolving agent in a solvent to form a solution and cooling the solution to obtain a solid precipitate rich in d-trans-1,2-cyclobutane dicarboxylic acid. The d-trans dicarboxylic acid can thereafter be recovered from the crystals.

The processes of the present invention thus provide products which are rich in the desired d-trans isomer. As used herein, "rich" means that, of the trans-1,2-cyclobutane dicarboxylic content of the crystals, the d-isomer is greatly predominant. It generally comprises 80 percent or more of the trans isomer and it preferably contains more than 90 percent of the d-isomer. In the practice of this invention, the purity of the d-isomer exceeds 95 percent and is in some embodiments indistinguishable from the pure d-isomer.

All parts, percentages, proportions and ratios herein are by weight, unless otherwise indicated.

The resolving agent according to the present invention serves to precipitate and/or crystallize with the desired d-isomer of the dicarboxylic acid. A particularly preferred resolving agent according to the present invention is cinchonidine, also known as (8α, 9R)-cinchonan-9-ol. It is obtained from cinchona bark and is readily available commercially.

The present invention contemplates the use of a liquid vehicle in which the resolving agent and the racemic acid are soluble at one temperature, while the product formed by the d-isomer and the resolving agent is less soluble at a second temperature different from the first temperature. Aqueous liquid vehicles have been found to be well-suited to the practice of the present invention. While a variety of aqueous vehicles can be used, for reasons of final purity and economy of operation, it is preferred in certain embodiments to use water. The water can be obtained from common natural sources, or the water can be distilled or otherwise purified, as for example, by de-ionization with exchange resins.

The proportions of the racemic acid and the resolving agent can be varied over a range. The process has successfully been carried out with stoichiometric proportions, although a slight excess of the resolving agent or of the racemic acid can be utilized.

The temperatures utilized in dissolving the racemic mixture and the resolving agent are selected according to the solvent used and the resolving agent. Generally, the solvent is heated to permit quantities of the racemic acid and resolving agent readily to dissolve. Thereafter, the resulting solution is cooled to a lower temperature to induce crystallization or precipitation of the product formed by the resolving agent and the d-isomer.

When water is utilized as the solvent in certain preferred embodiments hereof, the water is heated to from 90° C. to boiling to expedite dissolution of the materials. Thereafter, the temperature is lowered to about 5° to 25° C. The water is cooled to room temperature or chilled to some temperature above the freezing point of the liquid to cause separation of the resolving agent and the d-isomer. Thus, when water is the solvent, dissolution is effected at 90° to 100° C. and crystallization is carried out at from 5° to 25° C.

The cooling can be carried out either by a rapid chilling with brine or other refrigerant, or it can be carried out by permitting the vessel containing the solvent and ingredients to set at ordinary room temperatures. The latter form of cooling is preferred in certain embodiments of the present invention, both because of economy in not requiring expensive refrigeration and because good crystal growth and separation from the liquid are obtained.

The crystals or precipitate formed can be separated from the mother liquor by conventional techniques, such as filtration, vacuum or pressure filtration, centrifugation, and the like. The remaining mother liquor is enriched in the l-isomer and accordingly provides a source of this enantiomer. After separation of the crystals from the mother liquor, the d-isomer is obtained by splitting the complex of resolving agent and d-isomer.

The splitting can be carried out by hydrolysis of the complex when cinchonidine is the resolving agent and water is the solvent. Thus, a base can be used to hydrolyze the complex. Strong alkalis are desirable, and the hydroxides of alkali metals and ammonia are especially useful. Preferred bases are sodium hydroxide and ammonium hydroxide. This will cause the cinchonidine to precipitate as a solid, and it can then be separated from the hydrolysis mixture by conventional techniques, as set forth above, for separation of the precipitate from the solvent in which the resolution has been carried out. The cinchonidine can be recovered and treated for recycling to the first step of the process.

After the resolving agent has been separated, the solution containing the d-acid material is then acidified to a pH of 2.5 or lower to restore the isomer to its acid form. The acidification is readily carried out with a variety of strong acids, and particularly with mineral acids, such as sulfuric or hydrochloric. In certain embodiments of the invention, concentrated hydrochloric acid is a preferred acidifying agent. The d-isomer acid is recovered from the acidifying solution by conventional techniques such as evaporation. It is preferred that the acid utilized be present in at least stoichiometric quantity up to about a 50% excess.

After evaporation of the acidifying solution, the dried residue is extracted with an organic solvent for recovery of the dicarboxylic acid. This removes any residuum of inorganic material, such as, for example, ammonium chloride arising from treatment with ammonia or ammonium hydroxide to free the d-isomer from the cinchonidine resolving agent.

Generally, organic solvents such as ketones, esters, and aliphatic ethers can be utilized. In order to obtain good separation, lower aliphatic ketones, desirably those alkyl ketones containing from two to five carbon atoms, are used. A preferred ketone in certain embodiments is acetone. The lower aliphatic esters are desirable, and those having a total of from three to six carbon atoms are preferred. In certain embodiments of the present invention, ethyl acetate is a preferred solvent. Lower halo-substituted aliphatic hydrocarbons, particularly chlorinated one and two carbon atom alkyl groups provide good results, as do the lower alphatic ethers containing three to six carbon atoms, such as diethyl ether and the like.

The extraction can be repeated if necessary to remove virtually all of the d-isomer from any inorganic material. The extracting agent for the acid can then be removed by conventional techniques such as evaporation, vacuum evaporation, and the like.

The presently claimed process can be carried out in either a batch fashion or continuously, according to the production required. Those skilled in the art will recognize from the present description that apparatus can be adapted to the practice of this invention as required by the particular operating conditions. Similarly, the process can be carried out under sub- or superatmospheric pressure, but it is generally most economical to carry out the process under ordinary atmospheric pressure.

The reactants used herein are ordinary commercial materials. It has been found that greater purity of the dicarboxylic acids and the resolving agent results in better yields in the practice of the invention.

The d-isomer obtained according to the present invention is generally in a very high state of purity. The optical rotation of the cyclobutane dicarboxylic acid obtained is desirably at least +130°. The d-trans-1,2-cyclobutane dicarboxylic acid usually has a specific optical rotation, measured at from 0.1 to 1 g/100 ml of water, equal to or greater than +145°. Generally, the $[a]^D_{20}$ under these conditions is at least +150°.

The following Examples are given to illustrate embodiments of the invention as it is presently preferred to practice it. It will be understood that these Examples are illustrative, and the invention is not to be considered as restricted thereto except as indicated in the appended Claims.

EXAMPLE 1

A beaker is charged with 75 ml of water; the water is brought to a boil, and 2.88 g (0.02 moles) of racemic cyclobutane dicarboxylic acid and 5.9 g (0.02 moles) of l-cinchonidine are dissolved in the boiling water. After complete dissolution of the solids, the solution is permitted gradually to cool to room temperature (21° C.).

The crystals which form upon cooling are removed from the supernatant solution by filtration and redissolved in 50 ml of boiling water. After the solution is cooled to room temperature, long crystalline needles form. These are removed from the supernatant liquid by filtration.

The needles are re-suspended in water and sufficient 10% aqueous sodium hydroxide is added to bring the liquid to pH 10. This causes hydrolysis and the cinchonidine precipitates. The solution is filtered to remove the cinchonidine crystals.

The filtrate is then acidified to pH 2 with concentrated hydrochloric acid to provide the free acid, and the solution is evaporated to dryness. The resulting solids are extracted with ether, and the ether extract is evaporated to provide solid (1S,2S)-1,2-cyclobutane dicarboxylic acid.

The $[a]^{20}{}_D$ of the product at a concentration of 110 mg in 10 ml of water is $+137°$. This corresponds to 88.5 percent enantiomeric excess, the pure material having an optical rotation of about $+155°$.

EXAMPLE II

A two-liter beaker containing one liter of boiling water is charged with 28.8 g (0.20 moles) of racemic 1,2-cyclobutane dicarboxylic acid and 57.3 g (0.195 moles) of l-cinchonidine. After solution of the solids is complete, the beaker contents are permitted to cool to room temperature, whereupon crystals form.

The crystals are filtered from the mother liquor, placed in one liter of water, and redissolved by bringing the water to a boil. The resulting solution is then cooled to room temperature and the crystals which form are filtered off and redissolved in 700 ml of water, which is boiled.

After the water boils and the crystals have dissolved, the solution is allowed to cool to room temperature, so that crystals form. The crystals are separated from the mother liquor, suspended in 400 ml of water, and heated to 70°–80° C. Aqueous ammonium hydroxide solution (28%) is added to bring the pH to about 10 and thereby liberate the cinchonidine, and the resulting mixture is then boiled for five minutes and cooled to room temperature.

The cinchonidine which forms upon cooling is filtered off and the remaining liquid is extracted with chloroform to remove any remaining cinchonidine. The aqueous layer is thereupon acidified to a pH of about 1 with concentrated aqueous hydrochloric acid. The liquid is then heated gently to concentrate it to dryness.

The residue is thrice extracted with 100 ml portions of diethyl ether to separate the acid from the ammonium chloride formed during acidification. The combined ether extract is filtered and then concentrated to dryness to obtain 10 g of a white solid having an $[a]^{20}{}_D = +156°$ (at a concentration of 1 g/100 ml in water).

The product is recrystallized from boiling benzene to yield 9.8 of 1,2-cyclobutane dicarboxylic acid as shiny needles. The product has an $[a]^{20}{}_D = +154.8°$ (concentration of 1 g/100 ml water).

The d-trans-1,2-cyclobutane dicarboxylic acid so obtained is converted to 1-trans-1,2-bis(diphenylphosphinomethyl) cyclobutane, as per the method set forth in U.S. Pat. No. 3,949,000, which phosphino derivatives are used to prepare rhodium complex catalysts for the production of levamisole.

It will be appreciated from the foregoing that the racemic starting material includes that having low optical activity, as well as totally optically inactive material.

What is claimed is:

1. A process for preparing the d-enantiomer of trans-1,2-cyclobutane dicarboxylic acid which consists essentially in the steps of: dissolving racemic trans-1,2-cyclobutane dicarboxylic acid and cinchonidine in an aqueous solvent to form a solution thereof, cooling the latter solution, and recovering thus-formed crystals enriched in d-trans-1,2-cyclobutane dicarboxylic acid.

2. A process according to claim 1 wherein the crystals are recovered and hydrolyzed to provide a solution containing cinchonidine and the d-trans acid, separating the cinchonidine from the acid, and recovering d-trans-1,2-cyclobutane dicarboxylic acid.

3. A process according to claim 2 wherein the hydrolysis is carried out with a strong base.

4. A process according to claim 2 wherein the d-trans acid is recovered by extraction with an inert organic solvent thereof.

5. A process according to claim 4 wherein the inert organic solvent is chlorinated lower aliphatic hydrocarbon or an aliphatic ether.

6. A process according to claim 2 wherein the $[a]^{20}{}_D$ of the d-trans acid, measured at 1 g/100 ml of water, is at least $+130°$.

7. A process according to claim 1 wherein the solvent is water.

8. A process according to claim 7 wherein the solvent is boiling water, and the solution is cooled to a temperature below about 25° C.

* * * * *